(12) United States Patent
Daghighian

(10) Patent No.: US 7,750,311 B2
(45) Date of Patent: Jul. 6, 2010

(54) POSITRON EMISSION DETECTORS AND CONFIGURATIONS

(75) Inventor: Farhad Daghighian, Santa Monica, CA (US)

(73) Assignee: Intramedical Imaging, LLC, Los Angeles, CA (US)

(*) Notice: Subject to any disclaimer, the term of this patent is extended or adjusted under 35 U.S.C. 154(b) by 25 days.

(21) Appl. No.: 11/929,349

(22) Filed: Oct. 30, 2007

(65) Prior Publication Data

US 2008/0230704 A1    Sep. 25, 2008

Related U.S. Application Data

(63) Continuation-in-part of application No. 11/270,906, filed on Nov. 10, 2005.

(60) Provisional application No. 60/656,565, filed on Feb. 25, 2005.

(51) Int. Cl.
*H01J 1/08* (2006.01)

(52) U.S. Cl. .................. 250/398; 250/366; 250/367; 250/368; 250/369

(58) Field of Classification Search ............ 600/431, 600/407, 437
See application file for complete search history.

(56) References Cited

U.S. PATENT DOCUMENTS

| | | | | |
|---|---|---|---|---|
| 4,932,414 A | * | 6/1990 | Coleman et al. | 600/445 |
| 5,499,415 A | * | 3/1996 | McKenna | 5/601 |
| 5,961,457 A | * | 10/1999 | Raylman et al. | 600/436 |
| 6,776,527 B1 | * | 8/2004 | Tybinkowski et al. | 378/209 |
| 2003/0105397 A1 | * | 6/2003 | Tumer et al. | 600/436 |
| 2003/0189174 A1 | * | 10/2003 | Tanaka et al. | 250/363.03 |

* cited by examiner

*Primary Examiner*—Long V Le
*Assistant Examiner*—Joel F Brutus
(74) *Attorney, Agent, or Firm*—Koppel, Patrick, Heybl & Dawson; Michael J. Ram

(57) ABSTRACT

A three-dimensional detector module for use in detecting annihilation photons generated by positrons emitted from radio-labeled sites within a body is formed from multiple solid state photo-detectors attached to one or more scintillators. Each photo-detector can be attached to a scintillator to form a photo-detector/scintillator combination and multiple photo-detector/scintillator combinations can be arranged in an array. Alternatively, multiple photo-detectors can be attached to the surface of a single scintillator to form an array. Multiple arrays are then stacked to form a photo-detector module. The modules can then be assembled to form a sheet of photo-detector modules. Multiple sheets or multiple modules can then be arranged around a body to detect emissions from radio-labeled sites in the body. Multiple position sensors attached to the photo-detectors, arrays or modules provide the ability to locate the source of the positron emissions from the labeled sites in the body and generate an image of the emission site. A series of novel PET configurations can be constructed from these detector modules, making PET scanners portable, more sensitive and flexible to be used in numerous different operational configurations, such as operating room, emergency rooms, critical care units, or battlefield.

21 Claims, 9 Drawing Sheets

POSITRON EMISSION DETECTORS AND CONFIGURATIONS

This application claims benefit of application Ser. No. 11/846,469 filed Aug. 28, 2007 now converted to Provisional Application Ser. No. 60/999,771, and application Ser. No. 11/784,854, filed Apr. 9, 2007, which claims benefit of Provisional Application 60/855,829, filed Oct. 31, 2006 and Provisional Application 60/809,639 filed May 30, 2006 and is a Continuation-In-Part of U.S. application Ser. No. 11/270,906 filed Nov. 10, 2005, which claims benefit of U.S. Provisional Application Ser. No. 60/656,565, filed Feb. 25, 2005.

The devices are novel detector modules for positron emission tomography (PET) that utilizes a novel photodetector referred to as solid state photomultiplier. This module can accommodate small cubical scintillator elements that are symmetrical in all three directions. This enables development of novel detector configurations for PET scanners that are more compact, conforming to the patient's body, and having higher sensitivity and uniformity. By combining position tracking systems with these modules intra-operative PET scanning can now be performed.

BACKGROUND

Positron emission tomography (PET) is becoming a powerful modality to image cancer and other disease. It is the most accurate non-invasive method for measuring the concentrations of radiolabeled tracers in different locations of the body. PET is capable of imaging and measuring the concentrations of a particular biochemical, which in turn provides important physiological parameters in specific locations or organs. PET is an imaging modality that provides biochemical and physiologic information, whereas CT scans or MRI provides anatomical or structural information (Daghighian F, Sumida R, and Phelps M E.: "PET Imaging: An Overview and Instrumentation" *J. Nucl. Med. Tech.* 18. 5 (1990)).

The basic principle behind PET is that positrons emitted by positron emitting isotopes find an electron and annihilates to two identical photons that travel in opposite directions. The patient is injected with a positron emitting radio-pharmaceutical, such as F-18 labeled flourodeoxyglucose. This radio-pharmaceutical accumulates in the cancer tissues in amounts greater than other tissues. The patient is surrounded by a ring of detectors that are tuned to detect the annihilation photons of the positron-electron annihilation that occurs in the regions where the radio-pharmaceutical is concentrated. Therefore the positron emission is detected based on the detection of two annihilation photons by gamma ray detectors of the PET scanner. The computer portion of the PET scanner records the location of the two detectors that were hit by such photons within a time window of a few nanoseconds (coincidence time window). This coincidence detection of the annihilation photons is an essential part of the positron emission tomography. The position of the positron source is on the line that connects these two detectors, called the "line of response". The collection of these lines of response allows tomographic reconstruction of the distribution of the radio-pharmaceuticals in the body of the patient, forming the PET images.

Most of the basic elements of biological materials have positron-emitting isotopes (e.g., C-11, N-13, O-15, F-18, I-124). More than 500 biochemicals have been labeled with these isotopes (e.g., amino acids, fatty acids, sugars, antibodies, drugs, neuroreceptor ligands, nucleoside analogues, etc). PET not only provides distribution images of the tracer, but by repeating PET imaging at different times the kinetics of the tracer can be studied. By using an appropriate model, many important physiological parameters can be measured non-invasively at specific locations inside the body.

One of the problems of the current PET designs is the degradation of the spatial resolution away from the axis due to the penetration of the 511 keV photons (the Depth of Interaction or Parallax Problem). In order to reduce this effect, the diameter of the scintillator ring diameter of the standard PET scanner is taken to be larger than the useful field-of-view (FOV) (e.g. 83 vs. 64 cm, for Siemens' ECAT EXACT scanner; and 15 vs. 12 cm for Siemens' microPET scanner). This extra large diameter reduces the sensitivity and increases the cost due to the need for more detector material and associated electronics compared to a system with a smaller diameter. Another problem experienced by PET scanner that causes blurring of the images is the inter-crystal scatter of the annihilation photons.

The preferred basic element of the novel detector module disclosed herein is a photo-detector referred to as a Solid-State Photomultiplier (SSPM), or Silicon Photomultipliers (SiPM). Introduced in 2002, SSPMs have so far been used mainly in high energy and astrophysics experiments where very high sensitivity light detection is required. Such a device is a large assembly of micro pixel diodes operating in a binary mode. Each detector consists of an array of approximately 600 micropixels connected in parallel. The micropixels act individually as binary photon detectors, in that an interaction with a single photon causes a discharge. Each micropixel "switch" operates independently of the others, and the detector signal is the summed output of all micropixels within a given integration time. When coupled to a scintillator, the SSPM detects the light produced in the scintillator by incident radiation, giving rise to a signal proportional to the energy of the radiation. SSPMs have many advantages over photomultiplier tubes (the current standard for scintillation-based detection of radiation). An important advantage is that the operating voltage for SSPMs is around 50 V, as opposed to the kilovoltages required for PMTs, yielding a clear safety advantage for devices to be used inside the body. SSPMs are also extremely small—a 1×1 mm$^2$ detector performs comparably to a PMT with a 1 cm diameter and 5 cm length. SSPMs have an extremely fast signal rise time (~40 ps), high gain (~10$^6$), good quantum efficiency at 580 nm (>20%), high stability, and low dark current at room temperature. Buzhan P, et al. *Nuc. Inst. Meth. Phys Res A,* 504, p 48-52 (2003).

SUMMARY

Disclosed herein is a detector module that allows a reduction in the diameter of the system, and at the same time will maintain the spatial resolution across the transverse field of view (FOV). A benefit of this system is a significant improvement in system sensitivity, without the trade-off in spatial resolution.

The preferred basic detector element is a Solid State Photomultiplier (SSPM) or Silicon Photo-multiplier (SiPM) operating in conjunction with scintillation crystals, such as lutetium oxyorthosilicate (LSO). A detector module is built by connecting a two dimensional array of these detectors (e.g.; 8×8) to a sheet of scintillation crystals (referred to as a scintillator), for example a 3 mm thick sheet of LSO, by stacking several of these arrays, to form a three-dimensional detector module, thereby eliminating the depth of interaction problem since the depth of the crystal is divided into several segments and therefore measurable. Alternatively, each SSPM can be connected to an individual piece of scintillator, forming a SSPM-Scintillator component, and then by stacking these one piece SSPM-Scintillator components in three dimensions (for example 8×8×8) a detector module can be built. This second configuration makes it possible to identify inter-detector scatter events and assign these events to the most likely primary detector of interaction in such a way that the detection efficiency is improved and resolution losses are minimized. This way both of the problems with existing PET designs are eliminated without the need to increase the diameter of the detector ring.

Furthermore, multiple numbers of these modules can be formed into novel configurations and PET scanners with unique capabilities can be constructed. For example, PET scanners can be construct that are non-circular and the detector arrays can be conformed to the shape of the patient, thereby increasing the sensitivity. Another possible configuration is a PET scanner for use in the operating room, incorporating an array of detectors fixed under the bed or operating table where the patient is placed and one or more smaller arrays can be held by hand and moved over or around the other sides of the patient. The position of the one or more moving modules is recorded either by a wireless tracking system of position sensors, or by an articulating arm with encoded potentiometer joints. All the lines of responses that are recorded for each position of the moving array are then used to reconstruct a three-dimensional image of the radioactive distribution emanating from the site within the patient's body where the radio-pharmaceutical has accumulated.

(Rubashov, I. B., (U.S. Pat. No. 6,946,841)) proposes the application of hybrid photo-detectors (HPD) in a small field of view PET scanner that can work in high magnetic fields of an MRI scanner. This patent does not show or suggest the use of SSPMs which are totally different from HPDs (HPDs operate at around 1000 Volts). It also does not teach the 3D detector module incorporated in the invention described herein or the PET configurations that can be formed using these modules.

Ziegler et al. built a PET scanner for imaging animals called the Munich Avalanche Diode PET (MADPET-II) that utilizes avalanche photodiodes (APD's) in two concentric rings and provide some degree of depth of interaction information. Ziegler et al uses only two layers of detectors in the radial direction. The inner one has LSO crystals with the length of 8 mm and the outer ring's LSO crystals are 6 mm long. The side dimensions of LSO's are 2×2 mm (David P. McElroy, Wendelin Pimpl, Bernd J. Pichler, Magdalena Rafecas, Thomas Schüler, and Sibylle I. Ziegler, *IEEE Transactions On Nuclear Science*, 52, pp 199). They propose four different ways of correction for inter-crystal Compton scatter and test them utilizing Monte Carlo simulations. Their system is different from that described herein. The detector they use is an APD that requires several hundred Volts vs. 40 Volts for SSPM and APD's have a gain of a few hundred vs. the gain of SSPM that is one million. The two solutions described herein for inter-crystal Compton scatter is also different from those discussed by Zeigler. The technique set forth below uses the point of interaction with less energy as the first point of interaction and therefore the point to be used for calculating the line of response based on M. Rafecas, G. Boning, B. J. Pichler, E. Lorenz, M. Schwaiger, and S. I. Ziegler, "Inter-crystal scatter in a dual layer, high resolution LSO-APD positron emission tomograph," *Phys. Med. Biol.*, 48, pp. 821-848, (2003)) particularly page 824 and 825. Zeigler makes an improper assumption and proposes using the crystal with the higher energy as the point from which the line of response is calculated.

Ladebeck, et al. teach a Combined MR/PET system (U.S. Pat. No. 7,218,112) which can be constructed using a variety of detectors including silicon photomultiplier tubes (PMTs) (see line 8, column 2 and claim 15). A silicon photomultiplier tube (PMT) is different from silicon photomultiplier that does not have a tube. A silicon PMT is a hybrid semiconductor and PM-Tube, that is the same as an HPD and therefore different from SSPM. The reference fails to teach the 3D detector module or the various configurations disclosed by applicant herein.

M. Nagler et al., in a recent published United States Patent Application 2007/0156047 teaches systems, methods, and probes which are provided for functional imaging by radioactive-emission measurements which are specific to body structures, such as the prostate, the esophagus, the cervix, the uterus, the ovaries, the heart, the breast, the brain, and the whole body, and other body structures. The nuclear imaging may be performed alone, or together with structural imaging, for example, by x-rays, ultrasound, or MRI. Preferably, the radioactive-emission-measuring probes include detectors, which are adapted for individual motions with respect to the probe housings, to generate views from different orientations and to change their view orientations. These motions are optimized with respect to functional information gained about the body structure, by identifying preferred sets of views for measurements, based on models of the body structures and information theoretic measures. A second iteration, for identifying preferred sets of views for measurements of a portion of a body structure, based on models of a location of a pathology that has been identified, makes it possible, in effect, to zoom in on a suspected pathology. The systems are preprogrammed to provide these motions automatically. They fail to teach coincidence detection of the annihilation photons emitted by the positron emitting radio-isotopes that is the basis of PET imaging or show or suggest the novel PET detectors, modules, configurations and methods of PET imaging disclosed herein as incorporating applicant's inventions.

DETAILED DISCUSSION

Disclosed herein is a detector module assembly that allows a reduction in the diameter of a PET diagnostic system while, at the same time, allowing the operator to maintain the spatial resolution across the transverse field of view (FOV). One benefit of this system and arrangement of components described herein is a significant improvement in system sensitivity, without the trade-off in spatial resolution.

Figure 1:
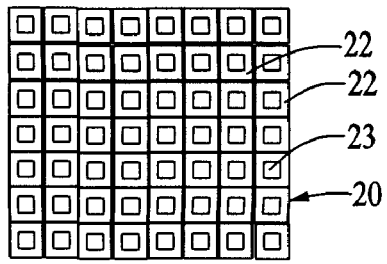
FIG. 1 is a top view of a two dimensional array of SSPM's consisting of 64 detectors each attached to a discrete scintillator or a sheet of scintillator.
Figure 2:
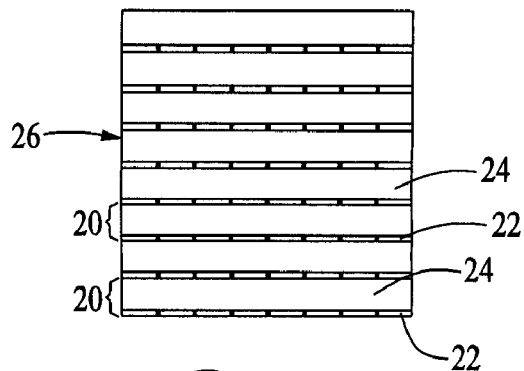
FIG. 2 is the side view of a detector module comprising eight SSPM arrays as shown in FIG. 1, with the detectors connected to a piece or sheet of scintillator, and then stacked on top of each other.

The preferred basic detector element used in the various embodiments described below is a Solid State Photo-multiplier (SSPM) or Silicon Photo-multiplier (SiPM) operating in conjunction with scintillation crystals, such as lutetium oxyorthosilicate (LSO). In the example shown in FIG. 1 a detector array 20 is built by connecting a two dimensional array of these detectors elements 22 to individual scintillators or a sheet of scintillators 24 to form an 8×8 array 20 of detector elements 22. Scintillation crystals 24, referred to as a scintillator, can be utilized as single scintillator elements, i.e. one scintillator element for each detector element, or as a sheet of scintillator, for example a 3 mm thick sheet of LSO. Several arrays 20 with detector elements 22 attached to scintillator 24 are stacked to form a three-dimensional detector module 26 such as shown in FIG. 2. Each SSPM (or SiPM) can be connected to an individual piece of scintillator, forming a SSPM-Scintillator component, an array 20 formed of these SSPM-Scintillator components, and then by stacking arrays of the one piece SSPM-Scintillator components in three dimensions (for example 8×8×8) a detector module 26 such as shown in FIG. 2 can be built. A similar configuration is obtained by attaching the detectors 20 to the sheet of scintillator 24 forming the array 20 and then stacking that array. This configuration of FIG. 2 makes it possible to identify inter-detector scatter events and assign these events to the most likely primary detector of interaction in such a way that the detection efficiency is improved and resolution losses are minimized.

Figure 5:
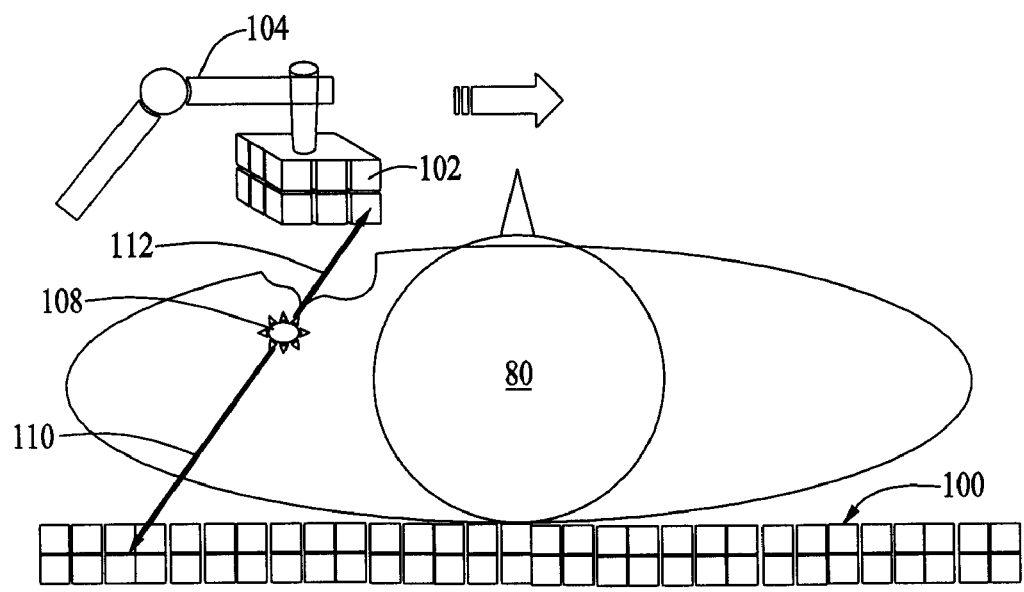
FIG. 5 is a schematic representation of a first embodiment of a PET scanner design incorporating features of the invention that is suitable for use in the operating room.
Figure 6:
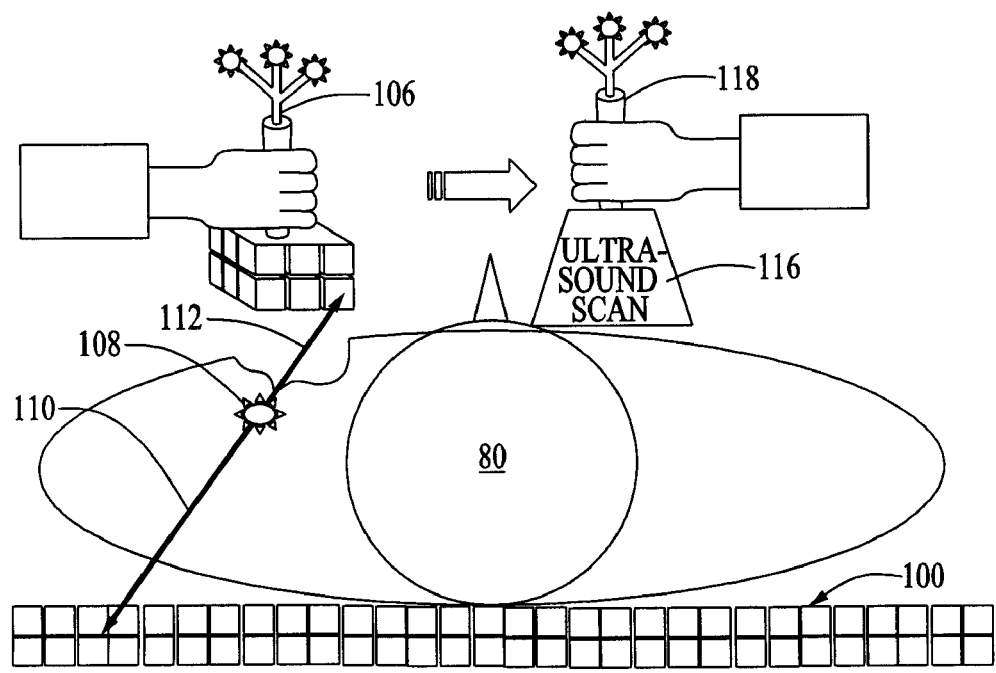
FIG. 6 is a schematic representation of a second embodiment of a PET scanner design for use in the operating room using a set of handheld detectors.

Furthermore, multiple numbers of these modules 26 can be formed into novel configurations, such as those described below and shown in FIGS. 5, 6, 10, 11, 12, 13 and 14 and PET scanners with unique capabilities can be constructed. For example, PET scanners can be construct that are non-circular and the detector arrays can be conformed to the shape of the patient or portions of the patient's body to be scanned, thereby increasing the sensitivity. Another possible configuration is a portable PET scanner for use in the operating room, or in patient room, critical care units, or emergency settings, such as shown in FIGS. 5 and 6, incorporating an array of detectors fixed under the bed or operating table where the patient is placed and one or more smaller arrays can be held by hand and moved in any desired increment or direction over or around the other sides of the patient. The position of the one or more moving modules and its positional relationship to the fixed modules is recorded either by a wireless tracking system of position sensors, or by an articulating arm with encoded potentiometer joints. All the lines of responses that are recorded for each position of the moving array are then used to reconstruct a three-dimensional image of the radioactive distribution emanating from the site within the patient's body where the radio-pharmaceutical has accumulated.

A first example of a module 26 of stacked arrays 20 comprises single SSPM detectors built by Hamamatsu that are ceramic mounted to provide a detector 22 which has a 2.4×1.9 mm face with a 1×1 mm active sensitive area 23. Each SSPM 22 is connected to a single scintillator piece 24, for example a 2.5×2.5×2.5 mm piece of LSO. One such array 20 comprises 64 SSPM's 22 arranged in an 8×8 array, such as shown in FIG. 1. The detector module 26 is then built by stacking eight of these SSPM-Scintillator arrays 20 on top of each other such as shown in FIG. 2. The scintillator is tapered to be matched with sensitive area 23, represented by the inner box in the center of each of the SSPMs 22.

Another embodiment that may be used is to connect an array of single photo-detectors 22, such as the same SSPMs as described above, to a scintillator plate 24, for example a plate of LSO which has a 20×20 mm surface and is 2.5 mm thick. In a top view this array 20 has substantially the same appearance as shown in FIG. 1.

A further alternative is a detector module 26 formed using an integrated array 20 of SSPM, each SSPM connected to a single scintillator 24. Commercial array modules of SSPM mounted on PCB with very little dead space between pixels, are available from SensL (Cork, Ireland). It is a tiled 4×4 array of SSPMs which features 3 mm×3 mm active regions separated by 100 micrometer channels. This increases the fill factor to almost 100%, and would improve the light collection. The readout electronics is built onto the chip to provide an analog signal output from each.

A still further alternative is a module 26 formed from an integrated array of photodetectors 22 connected to a scintillator plate 24 comprising LSO with the thickness of 2.5 mm. A stack of eight of such arrays 20 comprises the detector module 26.

Figure 3:
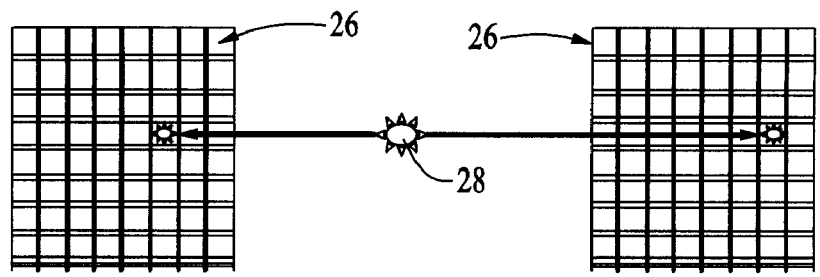
FIG. 3 depicts a pair of annihilation photons, emitted by a positron emitting radioisotope, being detected by individual scintillators on two spaced apart detector modules.
Figure 4:
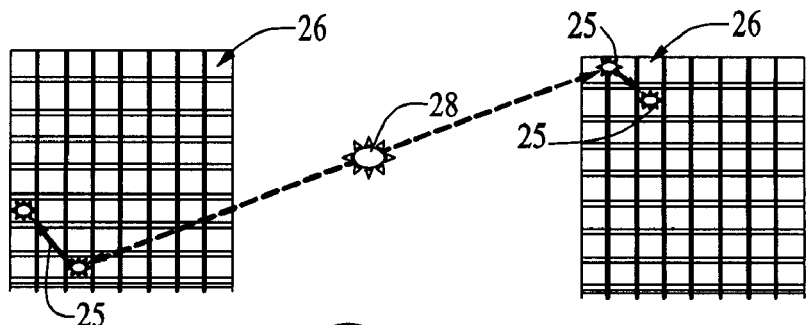
FIG. 4 is a depiction of a pair of annihilation photons being detected by individual scintillators of the detector module, both interactions being Compton scattering interactions that produce secondary gamma rays that are captured in other scintillators, depicting the inter-crystal scatter events.

Positron emission tomography is based on the simultaneous detection of the two annihilation photons that are emitted by the decay of a positron. Some of these annihilation photons interact with scintillator material either by photoelectric interaction, where they deposit all their energy. FIG. 3 depicts a pair of annihilation photons emanating from a source of positron emission. The source is spaced between two spaced apart detector modules 26 which include individual scintillators 24 such as described above. The subsequent annihilations 28 are detected by both modules. Both interactions are photo-electric interactions where all the energy of the photon is absorbed in the scintillator. As shown in FIG. 4, the annihilation photons can also deposit part of their energy in a scintillator piece 24 and then undergo Compton interaction 25 and generate other gamma rays that get detected in another scintillator piece 24. One or both interactions can be Compton scattering interactions, where part of the energy of the annihilation photon is absorbed in the primary scintillator (most of the time a smaller portion of the energy), and the rest of the energy (usually a larger portion of the energy) detected in other scintillators.

One of the many challenges in designing a PET system with small detector elements is the problem of Compton scatter in the detector material. Even when using high Z scintillator materials, such as BGO or LSO, only about 50% of the first interactions will result in a photoelectric interaction. The remaining interactions, will only deposit a portion of the primary photon energy in the initial detector. If the size of the detector is very small, there is high probability that the secondary photon will either deposit the remaining energy in a neighboring detector or escape the detector assembly altogether. For an annihilation photon having an energy of 511 keV, 50% of all interactions will result in a secondary scattered photon with an energy of 340 keV or higher, which corresponds to a scattering angle of 60° or less (i.e., forward scatter). When small detector elements are utilized it is very likely that these events will scatter out of the primary detector element and either deposit its energy in a neighboring detector or scatter out of detector assembly.

The amount of detector scatter is affected by crystal size and material, the spacing between crystals, the incident angle of the photons on the crystal, the type and configuration of photo-detectors used, the energy thresholds employed and the probabilities for photoelectric and Compton scatter interactions within the detector. Since a majority of the Compton scattered photons are forward directed, these types of inter-detector scattered events are most likely to occur at different depths in the detector module. One way to reduce these types of events is to use relatively shallow detectors, which will result in a loss in efficiency. On the other hand, if the detector has depth of interaction (DOI) capabilities, such as those described herein, these events can be captured, analyzed and assigned to the correct detector where interaction occurs, and the detector of first interaction can be identified for generation of line responses.

In high resolution PET systems a detector module often consists of an array of small scintillators coupled to individual or shared photodetectors. As the dimensions of the scintillator elements decreases, inter-crystal scatter increases due to the inability of the crystal element to capture the Compton scattered photon in the same detector element. This corresponds to a greater amount of crystal misidentification, inaccurate image quantification, and possible degradation of spatial resolution. If the system has individual photo-detectors attached to each detector element the processing of these inter-crystal scattered events, will primarily be determined on the setting of the energy discriminators. If a high energy threshold is used, the relatively small energy deposition in the primary detector will be rejected, and if the scattered photon is detected in an adjacent crystal element, the event is likely to be accepted and result in a mis-positioned event. As the energy threshold is lowered, more of the Compton interactions in the primary detector will be accepted together with the scattered events detected in the neighboring detector. These types of triple events can be treated in a number of ways. The event can be entirely rejected, which will result in a loss in detection efficiency but the loss in spatial resolution is minimized. The event can be randomly assigned or weighted according to the energy to one of the detectors, which will improve the detection efficiency, but with a loss in spatial resolution. The loss in resolution can be reduced with maintained detection efficiency if the energy depositions in the detectors and the probabilities of scattering angles (i.e., Klein-Nishina cross sections) are considered in the selection of the primary detector in which the photon interacts. Monte Carlo studies have shown that the detection efficiency of the system can be significantly improved without a significant loss to detector scatter if these triple events are properly handled by the detector logic.

One of the advantages of the detector configurations described herein is the possibility of localizing the points of Compton interactions. This information can be used to potentially improve detection efficiency by accepting multiple crystal events and/or remove image blurring that is present in all existing PET designs. Different algorithms for handling inter-detector scatter can be used such as:

1. Selection of the detector element based on comparing the energy depositions in the detector elements, assuming the lowest energy deposition is the primary detector (since forward scattering is more probable), or positioning of the event weighted inversely based on the energy deposited in the detector element (the event would be closer to the detector element that detected lower energy); or 2. Including knowledge of the source location, the location of the detector elements involved (scattering angles), and Compton scattering kinetics to select the most likely primary detector element.

As shown in FIGS. 5 and 6, the coincidence events can be recorded between the detectors under the patient in one hand, and the detectors on the moving modules above the patient. An array 100 of multiple detector modules 26 are located under, in or on the patient's bed, a set of movable detector modules 102 are placed above the patient 80 such that it's position is repeatedly measurable either by a position encoded mechanical arm 104, or by a remote position sensor, such as optical position trackers 106, wireless or electromagnetic position trackers 118 shown in FIG. 5.

Figure 7:
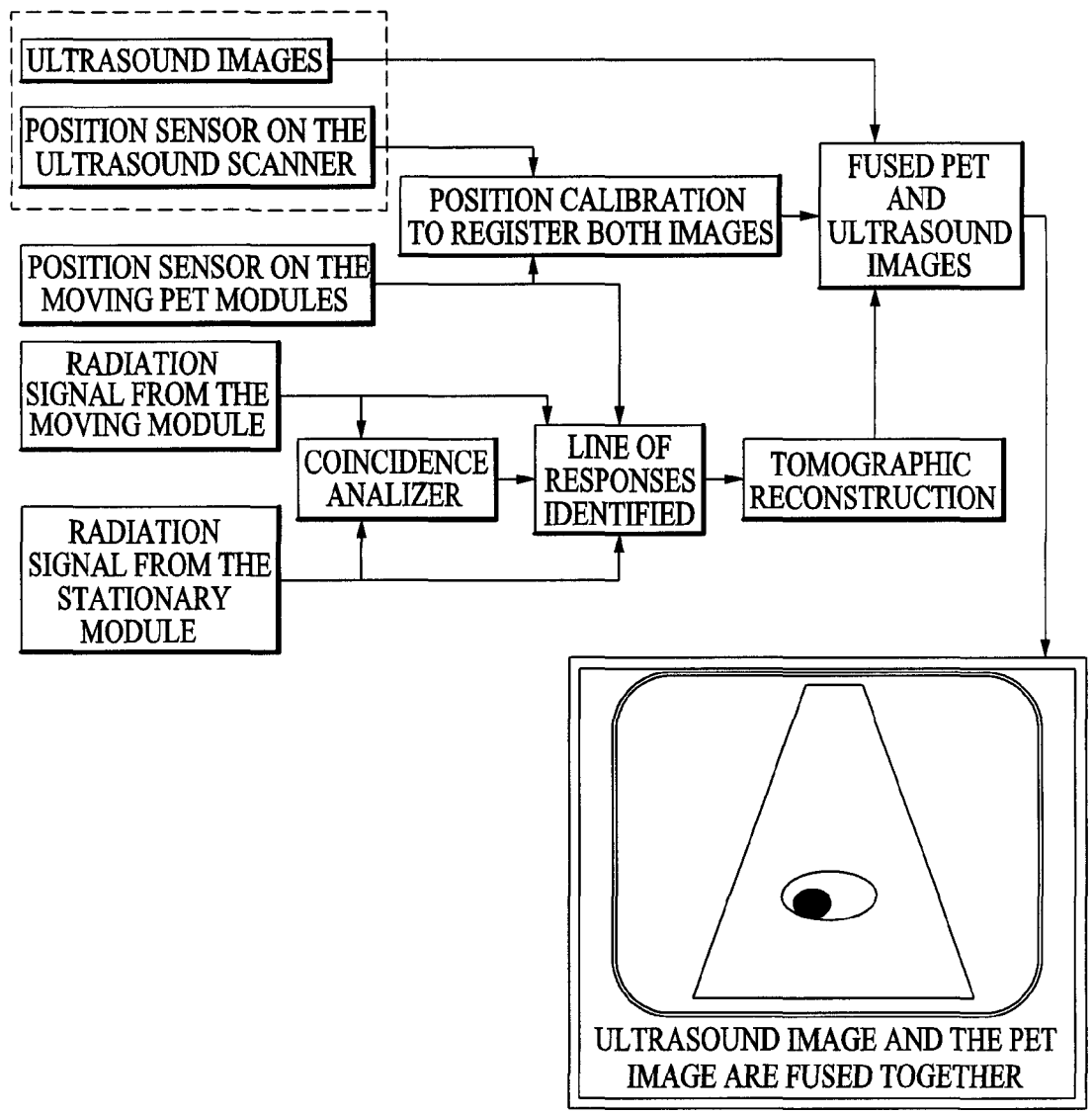
FIG. 7 is a diagram showing the flow of signals from the multiple detectors and position tracking devices on the detectors.

In order to generate a positron emission tomogram of a distribution of radio-isotope 108, the signals 110, 112 generated by the detection of the annihilation photons of the positron decays from the radiation sources 108 are fed into a coincidence analyser 114 (see FIG. 7). FIG. 6 shows a system that includes an ultrasound scanner 116 that also has its position tracked either by an encoded mechanical arm 104 or by a tracking system such as a wireless position tracker 118. The intra-operative ultrasound scanner can provide anatomical images which can be fused to the PET images.

FIG. 7 shows the flow of signals from the multiple detectors and the detector position tracking devices. Once the initial positions of the sensors are calibrated to a fixed point located within the operative location the data generated is used to assemble images of the radiolabeled tissue in the patient being diagnosed or receiving surgical treatment in an arrangement such as described and shown herein in regard to FIGS. 5 and 6 as well as the other arrangements described below. One embodiment of the system shown in FIG. 6 uses both an ultrasound scanner and moving PET modules as described above. This allows an ultrasound image to be superimposed on the PET image.

Numerous different position trackers described in the art include but are not limited to optical tracking systems, magnetic tracking systems, mechanical or robotic arm based tracking systems, radio-wave based tracking systems, soundwave based tracking systems, etc. or an internal tracking system, including for example, accelerometer based tracking systems, potentiometer based tracking systems, etc. or any combination of external tracking systems and/or internal tracking systems. The same configurations can be implemented with the patient in a seated position; one set of detectors are on the back of the patients and the other set is in front of the patient. This scanner has a much smaller foot-print and can be put in a smaller vehicle as a mobile PET and also would require less space in a hospital or clinic.

Figure 8:
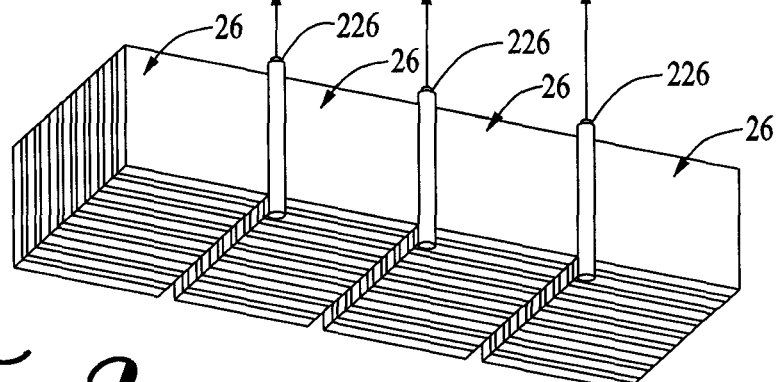
FIG. 8 is a perspective view of four detector modules mechanically connected by an angle measuring system.

FIG. 8 shows four detector modules that are mechanically connected by an electronic angle measuring system. The positions of all the detectors can be uniquely identified by measuring these angles and the position of the first detector on the chain. Each module 26 is mechanically connected to another via a pivot 226 that has means to measure and report the angle between the modules repeatedly, such an encoded potentiometers (not shown). This way a "chain" of detector modules 26 can be formed.

Figure 9:
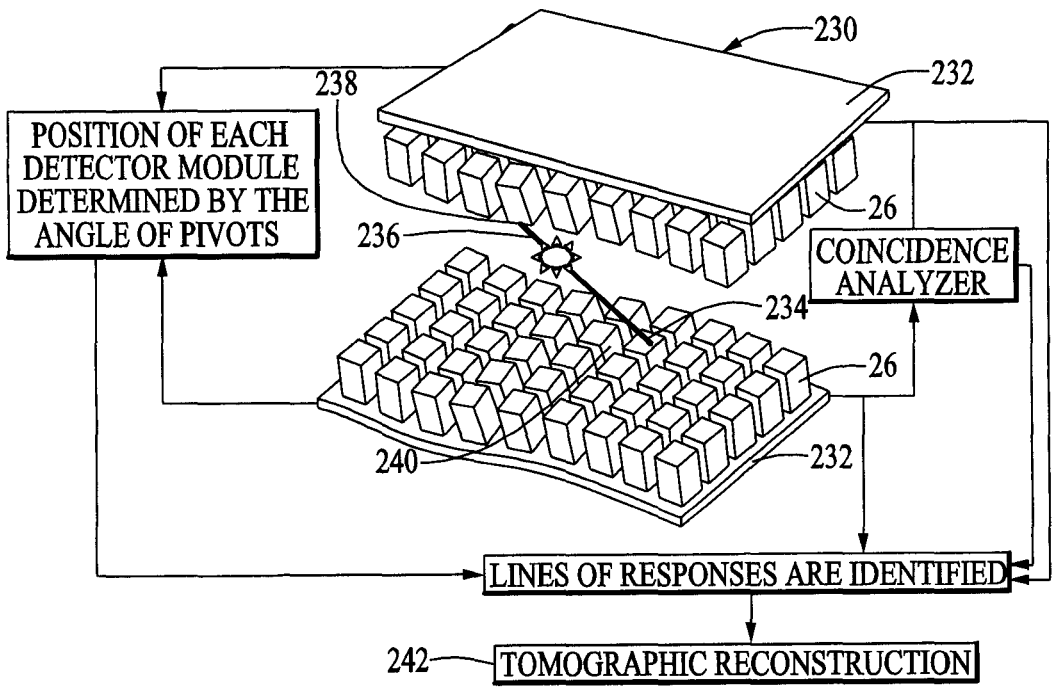
FIG. 9 is a schematic representation of two sets of flexible detector modules with two annihilation photons being detected by the detectors within the two detector modules.

An assembly 230 of several of these chains on a flexible membrane 232 is shown in FIG. 9. The encoded pivots 226 between each "chain" results in an assembly 230 comprising a semi-flexible "sheet" of detector modules 26. The position of each detector module 26 is determined by the data received from the pivots 226. In order to generate a positron emission tomogram of a distribution of radio-isotope 232, a second assembly 230 of the detector modules 26 is placed on the opposite side of the radioactive sources 232. The signals generated by the detection of the annihilation photons 234 and 236 of the positron decays from the radiation sources 232 are fed into a coincidence analyser. The positions of the detectors 238, 240 that were hit by these annihilation photons had been already recorded by the position sensors on the pivots 226 and sent to the computer 242 to form the tomographic images of the distribution of radioactivity.

Figure 10:
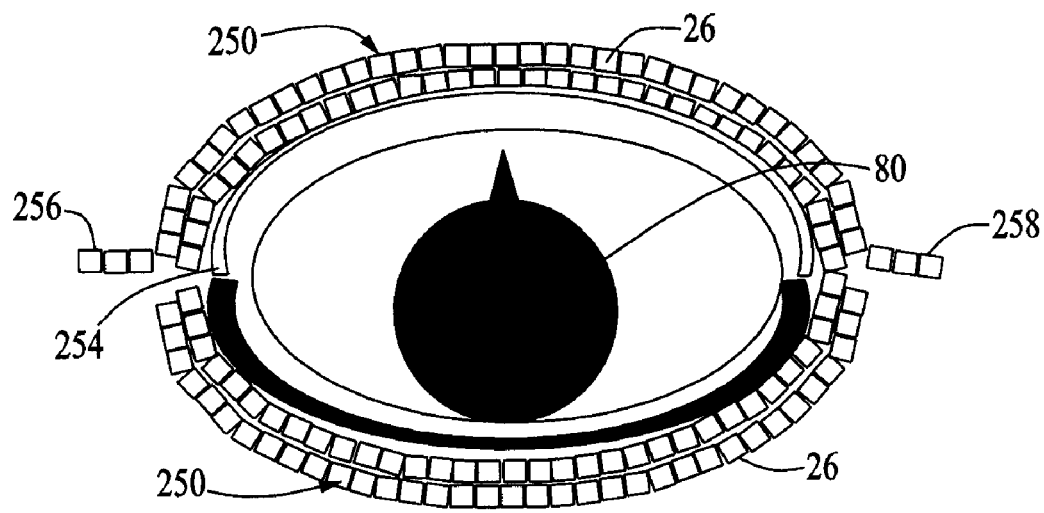
FIG. 10 is a schematic representation of a further embodiment showing an assembly of detector modules in a PET scanner where a set of detector modules are attached below the patient's bed and another set of flexible modules positioned over the patient.

Numerous novel PET assemblies can be built by utilizing these assemblies 230 which comprise rigid or semi-flexible "sheets" of detector modules 26, such as those listed below:

As shown in FIG. 10, a first assembly 250 of detector modules 26 are fixed below the patient's bed and a second assembly 250 of the semi-flexible "sheets" of the detector modules 26 are placed on top of the patient supported by a rigid plastic arch 254 so that the detectors 26 are located close to the patient's surface. Unused parts 256, 258 of the detector sheet may hang from both sides. These detectors at the edges may be disabled during the PET scanning. The advantage of this configuration over the conventional circular one-size-fit-all PET systems is that the sensitivity is significantly increased for skinny patients.

Figure 11:
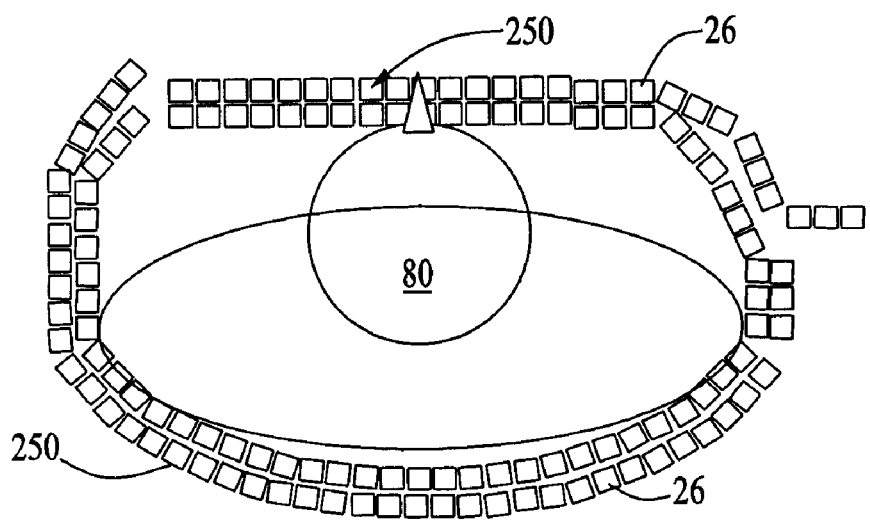
FIG. 11 is a schematic representation of a further embodiment showing an assembly of detector modules surrounding a patient that is sitting on a chair, viewed from the top.

FIG. 11 shows an embodiment with an assembly of the detector modules 26 around a patient seated on a chair. One assembly 250 of detector modules is on the back of the patient's chair. Other assembly or assemblies 250 of detector modules 26 are placed in front and on the sides of the patient during the scanning. Because the patient is in a sitting position he or she can do physical activity such as stationary bicycle to increase the heart rate.

Figure 12:
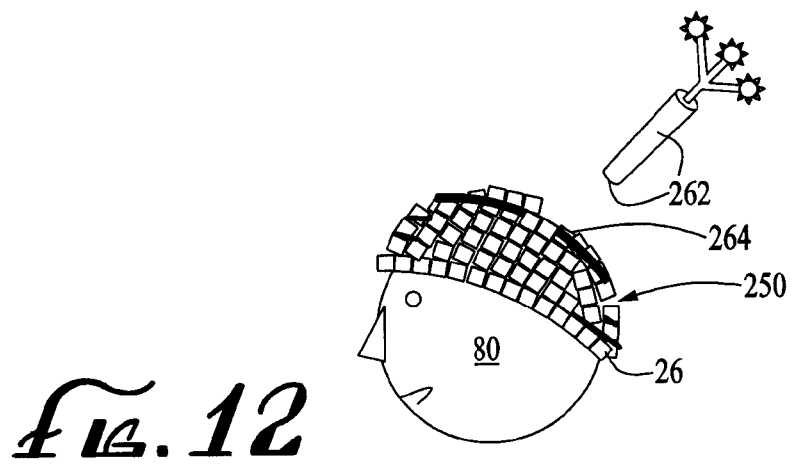
FIG. 12 is a schematic representation of an embodiment of a PET scanner comprising an assembly of detector modules for imaging of the brain.

FIG. 12 shows an embodiment with an assembly 250 of detector modules 26 wrap around an organ, such as the head to scan the brain, thus providing a portable system. If the assembly 250 is flexible it can be adjusted to the size of the organ being evaluated. Interventional instruments 262, such as biopsy needles, radiation therapy instruments, syringes for injection of therapeutic or diagnostic compounds, therapeutic ultrasound generators, radio-therapy devices, cryogenic instruments, radio-frequency antennas, can be inserted, for example, through small holes 264 in the assembly 250 and into the organ being examined in real-time under the guidance of PET images. Radioactive markers can be attached to these needles to track them in the PET images, or position sensors 266 can be attached to them to enable the tip of the instrument 262 to be tracked in the PET images. Such a configuration can be built with a non-flexible assembly 250 as well.

This mobile and compact head PET scanner can be used in emergency medicine, such as in a battlefield or trauma situation, to determine if the patient is having a head trauma or internal bleeding. It can also be used for assessing the status of an injury to other parts of the body such as an injured hand or leg. A radio-isotope with relatively long half-life that emits positrons, such as I-124 with 4.2 days half life, labelling a compound that does not clear substantially from blood within the first hour after iv injection (such as Human Serum Albumin), can be used by the emergency crew. If there is hemorrhage in the brain for example, then the PET image will find it as an abnormal area of radioactive concentration in the brain. Similar structure can be used to evaluate trauma to other portions of the body.

Also, because the SSPM's that makes up the detector modules 26 are insensitive to magnetic field, this PET scanner can be used simultaneously with an MRI scan, and enable fusion of both images.

Figure 13:
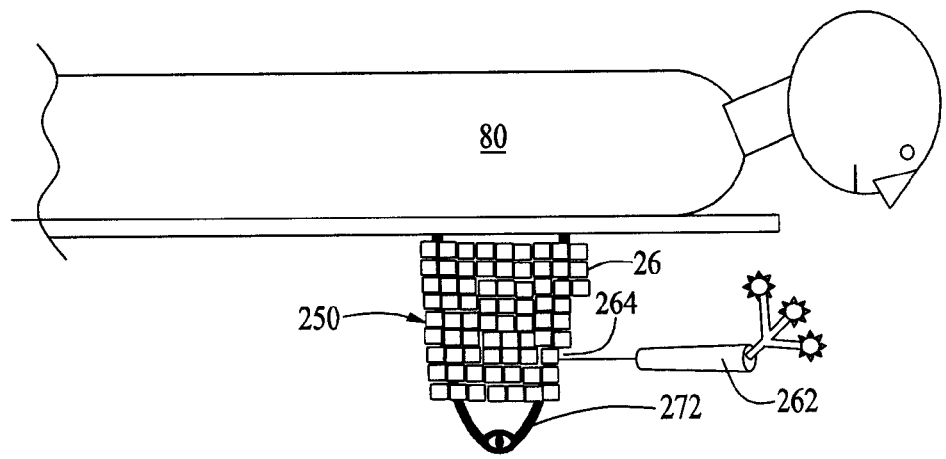
FIG. 13 is a schematic representation of a PET scanner comprising an assembly detector modules for imaging of breast.

As shown in FIG. 13, multiple assemblies 250 of detector modules 26 can be fixed around the breast 272 of a patient and a PET scan acquired. Various interventional instruments 262 can be inserted, for example through small openings 264 between the modules 26. As indicated above, radioactive markers can be attached to these needles to track them in the PET images, or position sensors can be attached to the instrument tip to enable the tip to be tracked in the PET images. The benefits of the assembly 250 described in regard to FIG. 12 also apply to the use shown in FIG. 13.

Figure 14:
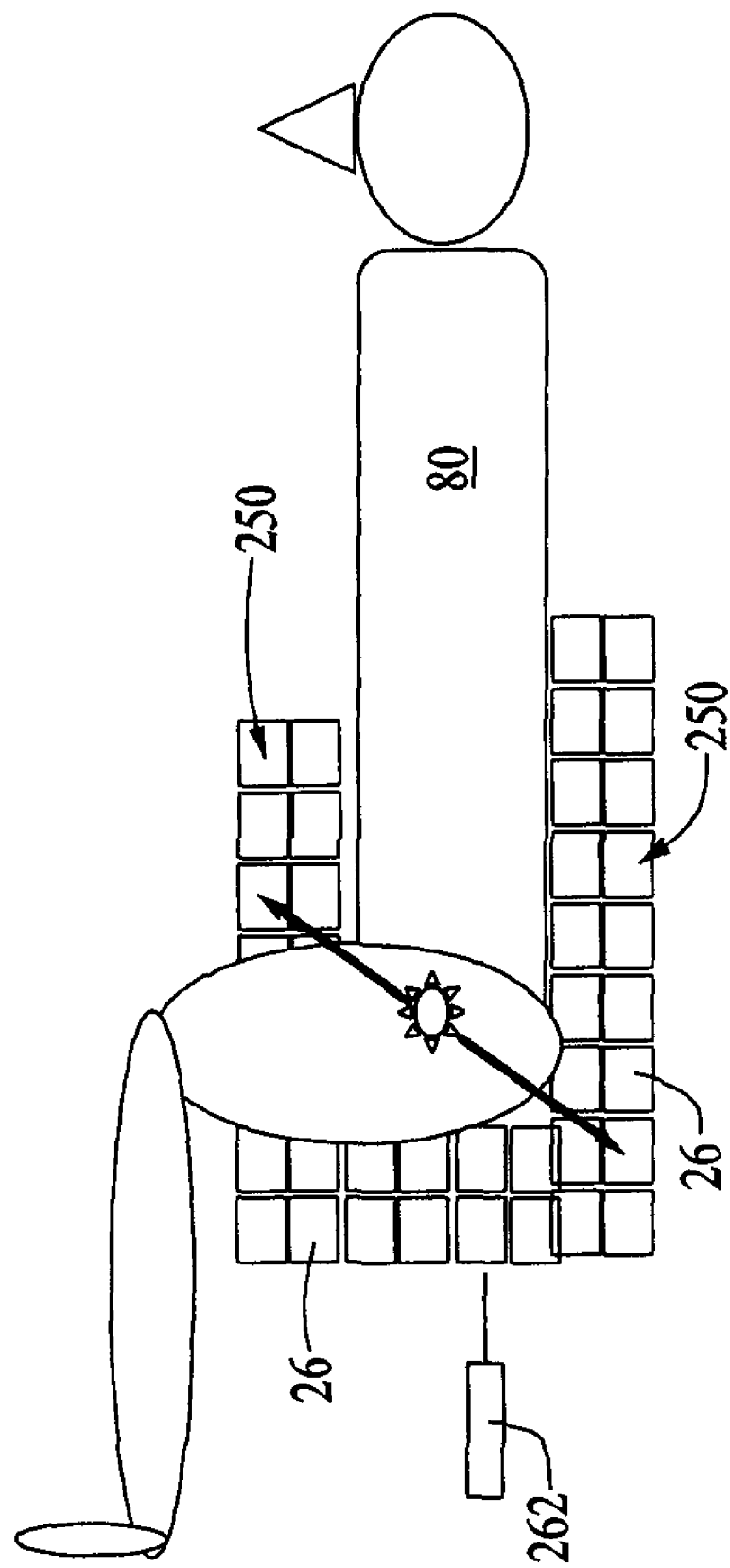
FIG. 14 is a schematic representation of an embodiment showing an array of detector modules placed under, on and around the patient's pelvis area to provide a PET scan during an interventional procedures such as a biopsy of the prostate or gynaecological organs, or the delivery of radiation, radio therapy, brachytherapy, cryosurgery, cryotherapy, medicinal therapy, gene therapy, minimally invasive surgery, cryo-surgery, or cell therapy.

As shown in FIG. 14 the assembly 250 of detector modules 26 can also be placed around the pelvic area to provide a PET image and perform various interventions. Various interventional procedures can be performed, such as biopsy of prostate or gynaecological organs, or deliver radiation, cryo, radio wave, ultrasound energy, lavage, medicinal, genetic, or cell therapy.

Figure 15:
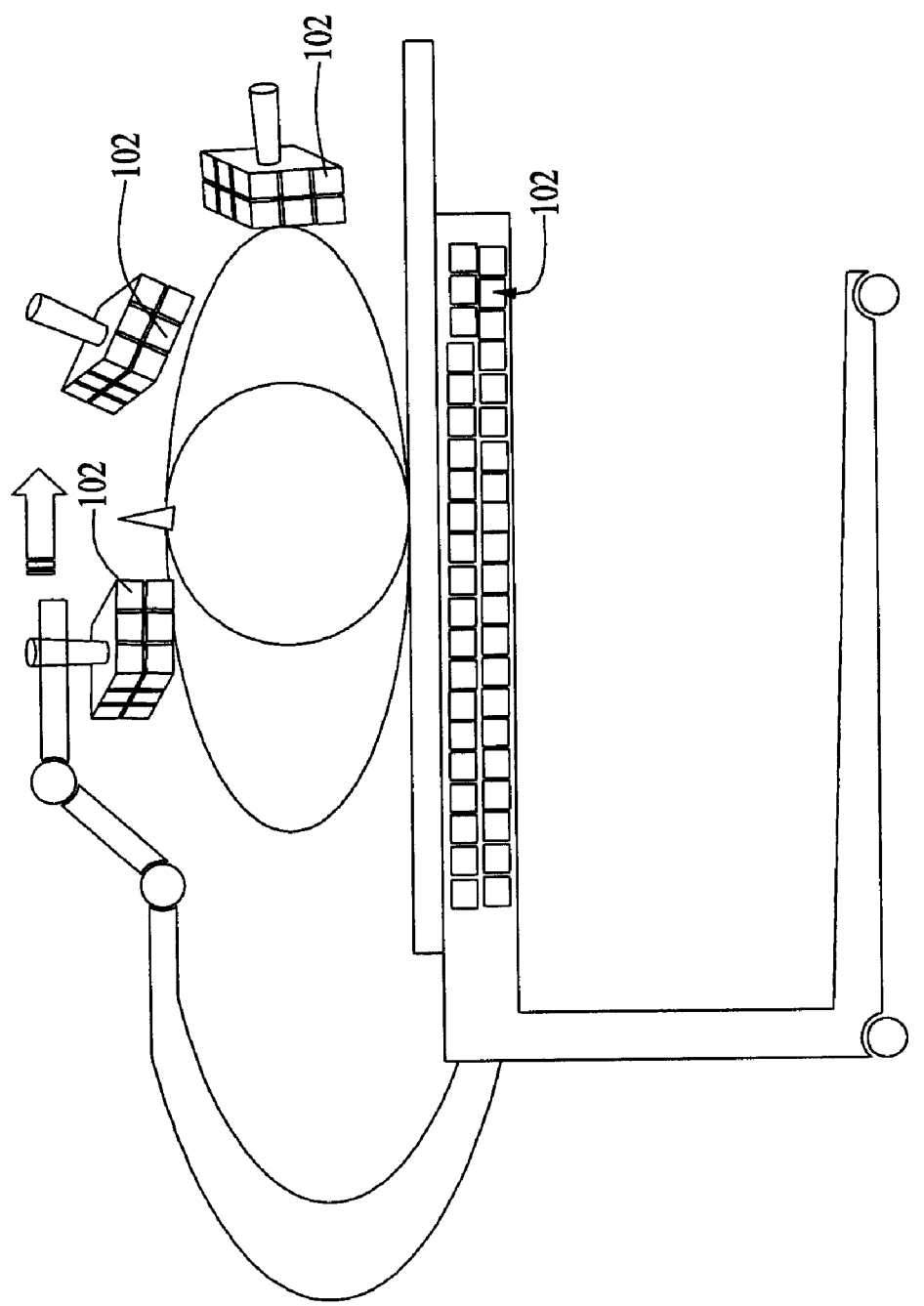
FIG. 15 is a schematic representation of an embodiment showing at least two arrays of detector modules facing each other at an adjustable distance, and being mobile for example by a set of wheels.

FIG. 15 is a schematic representation of an embodiment showing at least two arrays 100, 102 of detector modules facing each other at an adjustable distance, these arrays being mounted on a mobile, wheeled structure. This system is suitable for use in critical care units, emergency settings, and imaging patients in their rooms. The PET scanner assembly can be rolled to the patient's location similar to a mobile x-ray unit. FIG. 15 also shows two additional hand-held arrays 102.

Figure 16:
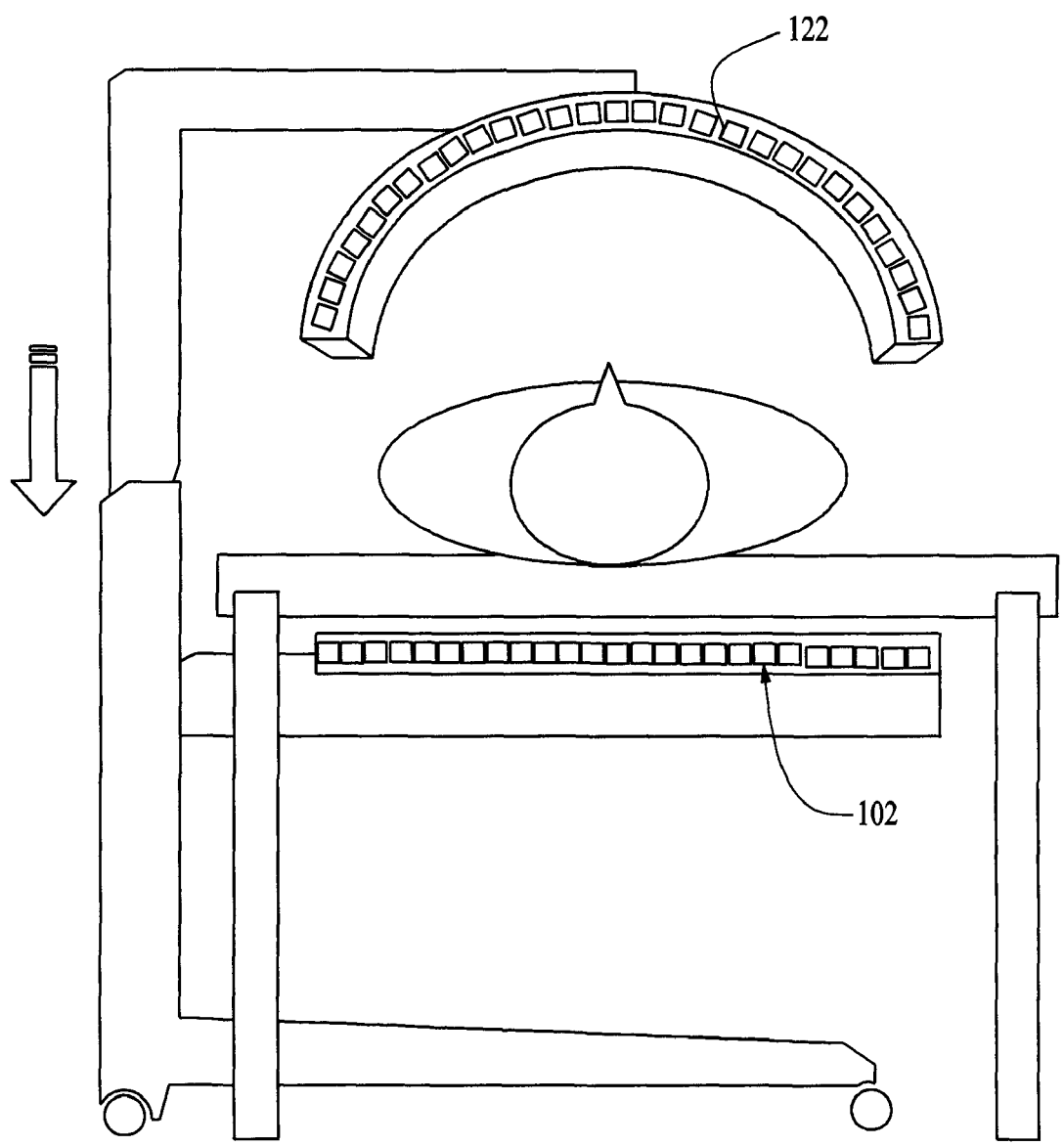
FIG. 16 is a schematic representation of another portable embodiment showing two arrays of detector modules.

FIG. 16 is a schematic representation of an embodiment showing at least two sheets 102, 122 of detector modules facing each other at an adjustable distance, these arrays being mounted on mobile, wheeled structures. This system is suitable for use in critical care units, emergency settings, and for imaging patients in their rooms. The PET scanner assembly can be rolled to the patient's location similar to a mobile x-ray unit.

Described herein are new arrangements and assemblies for assembling PET diagnostic devices that have enhanced capability, mobility and accuracy for detecting the presence of radiolabeled body components. Multiple SSPM detectors are assembled into an array, preferable comprising 64 detectors in an 8×8 arrangement with the SSPM's attached to a scintillator sheet. Alternatively, each SSPM has a discrete scintillator attached thereto. The SSPM with attached scintillator forms a detector array. Multiple arrays are then stacked, for example eight arrays, to form a 3-dimensional stacked array referred to as a detector module. These modules can then be assembled to form a sheet of modules. Individual detector, arrays or modules within the sheets further include devices to identifying the position, in relationship to a fixed point. This then allows the operator, through instrumental techniques, to identify the location of a gamma ray interaction within the sheet of detectors surrounding a patient positioned between surrounding sheets and, as a result pinpoint the source of positron emissions from a radiolabeled site within the body of the patient. Various different assemblies can be formed using the sheets of detector modules positioned in close proximity of the patient's body to allow for a broad use of PET diagnostics under conditions not previously available and with greater accuracy, speed, and reliability.

One skilled in the art will recognize that the utility of the detectors, modules and assemblies described herein are not limited to the examples presented. An unlimited variety of body portions can be surrounded by the assemblies of detectors and various different conditions observed, diagnosed and treated using the devices incorporating the inventions described therein. It should also be recognized that the utility of the invention extends to any tissue (i.e. tumors, blood vessels, lymph nodes) or body fluids (for example blood) that can be radiolabeled.

I claim:

1. A system for detecting positrons emitted from radio-labeled sites within a body, said system comprising a detector assembly therein for identifying the location of the radio-labeled site within the body, said detector assembly comprising one or more sheets of radiation detectors positioned around the body so as to intercept annihilation photons resulting from positron emissions from within the body, said one or more sheets of radiation detectors comprising:
   a) multiple silicon photomultipliers attached to one or more scintillators to form an array, said array constituting a plane,
   b) multiple arrays stacked in a direction perpendicular to the plane of the array to form a three dimensional radiation detector module, and
   c) multiple radiation detector modules arranged to form a two dimensional sheet of multiple radiation detector modules.

2. The system of claim 1 wherein at least a portion of the one or more sheets of multiple radiation detector modules are flexible.

3. The system of claim 2 including encoded pivots between adjacent radiation detector modules in the sheets.

4. The system of claim 1 wherein position tracking detectors are attached to multiple arrays or multiple radiation detector modules within the one or more sheets of multiple radiation detector modules.

5. The system of claim 1 wherein each silicon photomultiplier is attached to a scintillator to form a detector/scintillator combination, multiple detector/scintillator combinations being assembled to form the array, or multiple silicon photomultipliers are attached to a single scintillator to form the array.

6. The system of claim 1 further including supplemental diagnostic instrumentation such that an image display originating from the output of said supplemental diagnostic instrumentation can be combined with an image display originating from the output of said system for detecting positron emissions to provide a combined image of the location of the source of emissions.

7. The system of claim 6 wherein the supplemental diagnostic instrumentation comprises ultrasound diagnostic imaging instrumentation.

8. The system of claim 1 arranged for performing a diagnostic procedure on a patient comprising a first set of sheets of radiation detector modules positioned in one side of the patient and one or more sheets of radiation detector modules on the other sides of the patient, said system alternatively including one or more moveable radiation detector modules.

9. The system of claim 1 arranged for use for performing a diagnostic procedure on a seated or standing patient comprising a first sheet or sheets of detector modules positioned behind the back of a seated or standing patient and one or more sheets of detector modules along the sides of and in front of a seated or standing patient, said system alternatively including one or more moveable radiation detector modules.

10. A first three-dimensional detector module and one or more additional three-dimensional detector modules, each three-dimensional detector module providing detection of annihilation photon gamma rays emitted from positron annihilations of a radio-labeled sites within a body, said first three-dimensional detector module and one or more additional three-dimensional detector modules optionally including means therein or thereon for generating a position identifying signal, said first three-dimensional detector module and one or more additional three-dimensional detector modules when operated in combination, functioning to identify the location of the radio-labeled site within the body, each three-dimensional radiation detector module comprising
   a) multiple silicon photomultipliers attached to one or more scintillators to form an array, and
   b) multiple arrays stacked to form a detector module.

11. The first three-dimensional detector module of claim 10 wherein each silicon photomultiplier is attached to a scintillator to form a silicon photomultiplier/scintillator combination, multiple silicon photomultiplier/scintillator combinations being assembled to form the array, or multiple silicon photomultipliers are attached to a single scintillator to form the array.

12. The first three-dimensional detector module of claim 10 wherein sixty-four silicon photomultipliers are arranged in an eight by eight square, the sixty-four silicon photomultipliers are attached to one or more scintillators to form an array, and eight arrays are stacked to comprise a module containing five hundred and twelve silicon photomultipliers in an 8×8×8 cube.

13. A positron emission tomography scanner assembly comprising one or more sheets of radiation detectors for positioning around a body, said body having radio-labeled sites, the assembly positioned so as to intercept annihilation photons originated from positron emissions from within the body, said one or more sheets of radiation detectors comprising:
   a) multiple silicon photomultipliers attached to one or more scintillators to form an array,
   b) multiple arrays stacked to form a radiation detector module, and
   c) multiple radiation detector modules arranged to form a sheet of multiple detector modules position-locating devices optionally attached to at least some of the radiation detector modules, such that the location of electrical signals generated by radiation detectors or detector modules by interaction of annihilation photons emanating from positrons emitted in the body with scintillators attached to said silicon photomultipliers can be determined and multiple signals so detected can be analyzed to identify the position within the body of the source of said positron emissions.

14. The positron emission tomography scanner assembly of claim 13 arranged for use with a patient comprising a first sheet of radiation detectors positioned on one side of the patient and one or more sheets of radiation detectors positioned on the other sides of the patient, said scanner assembly alternatively also including one or more moveable detector modules.

15. The positron emission tomography scanner assembly of claim 13 arranged for use in performing a diagnostic procedure on a seated or standing patient comprising a first sheet of detectors positioned behind the back of the seated or standing patient and one or more sheets of detectors along the sides of and in front of the seated or standing patient, said scanner assembly alternatively also including one or more moveable detector modules.

16. The positron emission tomography scanner assembly of claim 13 arranged for placement only around a portion of a body being examined, said portion of the body comprising the head, breast, a limb or the pelvic region.

17. The positron emission tomography scanner assembly of claim 13 further including apertures therein for placement of diagnostic or procedural instrumentation there through.

18. The positron emission tomography scanner assembly of claim 17 wherein the diagnostic or procedural instrumentation comprises surgical tools, interventional instruments, therapeutic ultrasound generators, radio-therapy devices, cryogenic instruments, radio-frequency antennas, biopsy devices, or fluid or medication delivery devices.

19. The positron emission tomography scanner assembly of claim 18 wherein the diagnostic or procedural instrumentation includes at least one position tracking device, the position of the diagnostic or procedural instrumentation being shown on images generated by the scanner assembly.

20. The positron emission tomography scanner assembly of claim 18 wherein the diagnostic or procedural instrumentation includes at least one position tracking device, the position of the diagnostic or procedural instrumentation being shown on images generated by the scanner assembly.

21. The positron emission tomography scanner assembly of claim 13 further including a wheeled support structure so that the positron emission tomography scanner assembly can be moved to the location of a patient and positioned to surround only the portion of the body of the patient to be subjected to positron emission analysis.

* * * * *